(12) United States Patent
Gustafsson

(10) Patent No.: US 6,423,043 B1
(45) Date of Patent: Jul. 23, 2002

(54) ABSORBENT ARTICLES WITH IMPROVED BODY CONTACT

(75) Inventor: Anders Gustafsson, Billdal (SE)

(73) Assignee: SCA Hygiene Products AB, Gothenburg (SE)

(*) Notice: Subject to any disclaimer, the term of this patent is extended or adjusted under 35 U.S.C. 154(b) by 0 days.

(21) Appl. No.: 09/446,382

(22) PCT Filed: Jun. 18, 1998

(86) PCT No.: PCT/SE98/01188

§ 371 (c)(1),
(2), (4) Date: Dec. 21, 1999

(87) PCT Pub. No.: WO98/58614

PCT Pub. Date: Dec. 30, 1998

(30) Foreign Application Priority Data

Jun. 24, 1997 (SE) .............................. 9702394

(51) Int. Cl.⁷ .............................. A61F 13/15
(52) U.S. Cl. ............ 604/385.01; 604/378; 604/385.14; 604/385.16; 604/385.24; 604/385.31
(58) Field of Search ................. 604/378, 385.01, 604/385.14, 385.16, 385.24, 385.31, 387, 393

(56) References Cited

U.S. PATENT DOCUMENTS

| 3,570,493 A | 3/1971 | Olsson |
| 5,425,726 A | 6/1995 | Shimizu et al. |
| 5,853,403 A | * 12/1998 | Tanzer et al. ............ 604/385.1 |
| 6,296,628 B1 | * 10/2001 | Mizutani ..................... 604/387 |

FOREIGN PATENT DOCUMENTS

| EP | 0 067 465 | 12/1982 |
| GB | 862763 | 7/1961 |

* cited by examiner

Primary Examiner—John G. Weiss
Assistant Examiner—Michael Bogart
(74) Attorney, Agent, or Firm—Young & Thompson

(57) ABSTRACT

Absorbent article such as a sanitary napkin, a panty liner or an incontinence pad, includes a first absorbent part and a second part, which each have a substantially elongate shape with a longitudinal direction and a transverse direction, and two end portions. The two parts are mutually joined solely at their end portions. The second part is curved in the longitudinal direction and has high resistance to flexure along flexure lines parallel to the article's transverse direction both in a wet and dry condition, while the first part in a non-influenced condition has a lesser extension in a longitudinal direction than the second part and comprises at least one elastically extensible region in the longitudinal direction.

17 Claims, 3 Drawing Sheets

ABSORBENT ARTICLES WITH IMPROVED BODY CONTACT

CROSS REFERENCE TO RELATED APPLICATION

This is the 35 USC 371 national stage of International application PCT/SE98/01188 filed on Jun. 18, 1998, which designated the United States of America.

TECHNICAL FIELD

The present invention relates to an absorbent article such as a sanitary napkin, a panty liner or an incontinence pad, which article is intended to be substantially accommodated within a user's panties and comprising a first absorbent part and a second part, whereby both the first part and the second part have a substantially elongate shape with a longitudinal direction and a transverse direction, with each part presenting two end portions, whereby the two parts are mutually joined solely at their end portions.

BACKGROUND OF THE INVENTION

A basic requirement for an absorbent article such as a sanitary napkin or the like is that the article must be shaped in such a manner that it can collect and absorb all discharged bodily fluid.

Since, for example, sanitary napkins are intended to be accommodated within a pair of normal panties, they are relatively small and, above all, often rather narrow. There is therefore an obvious risk that by misplacing such an article within the panties or by it being deformed during use, it will not present a sufficiently large receiving surface for the discharged bodily fluid.

For example, it is not uncommon that the absorbent article is placed by mistake too far forward or too far backwards or offset somewhat transversely. Another commonly occurring reason for bodily fluid to leak past an absorbent article and to soil the user's clothing is that the article is compressed between the legs of the user and thus becomes so narrow that the surface available for absorption becomes insufficient. Neither is it unusual for the side edges of the article to become folded over the surface of the article, thereby reducing the available surface.

An absorbent article of the type under consideration is generally maintained in the panties of the user by means of self-adhesive glue and/or a friction coating. When placing the article in the panties, it is difficult to obtain a placement which is optimal in relation to the body of the user. Normally, the crotch portion of the panties is used to determine where the article is to be placed. However, since panties are manufactured in a surprisingly large number of different models and sizes, the position and shape of the central portion provides an extremely unreliable indication of where in the panties an absorbent article should be positioned.

Another reason why leakage arises in absorbent articles intended to be attached within the user's panties is that the article moves together with the panties rather than following the body movements of the user. This implies that when the user moves, the position of the panties and thus that of the absorbent article may be changed in relation to the user's body.

A further complication in connection with absorbent articles intended to be accommodated within a pair of panties is that the quality of the panties is often very poor. Many users of sanitary napkins or the like want to avoid ruining their best underwear through staining due to, for example, menstruation blood and therefore use old, worn-out panties with poor elastic and poor fit during the critical period. This of course increases the likelihood of a gap arising between the user's body and the absorbent article. There is therefore a clear risk that fluid may leak out between the body and the absorbent article.

Previously, it was common to attach absorbent articles such as sanitary napkins to a girdle which held the article in contact with the user's body. The advantage with such girdles was that the absorbent article, during use, was always in contact with the body and could intercept discharged liquid as soon as it left the user's body. The risk that liquid would leak out through gaps between the article and the user's body was thus minimal. However, the girdles were regarded by the users as being awkward and difficult to use and could be difficult to conceal under normal clothing. Today's users have become used to simply and quickly being able to attach the absorbent article within their panties and no longer accept the need to use girdles.

In order to reduce leakage which arises when absorbent articles are compressed between the user's legs, it has become customary to provide the absorbent articles with particular attachment flaps. By way of example, it is known from SE 455,688; U.S. Pat. No. 4,285,343; EP 130,848; EP 134,086 and U.S. Pat. No. 4,608,047 to provide sanitary napkins with flexible side flaps or wings which project from the longitudinal side edges. Such side flaps are intended to be folded around the leg openings of the user's panties during use and affixed to the outside of the panties. The side flaps themselves provide protection against side edge-leakage and staining of the panties. In addition, deformation of the absorbent body of the sanitary napkin is counteracted due to the fact that the napkin is fastened between the leg openings of the panties and, during use, is maintained in an extended state therebetween.

A considerable disadvantage with equipping absorbent articles with such attachment flaps is that many users feel that it is embarrassing that the attachment flaps, during use of the article, are visible on the outside of the panties. This also implies that absorbent articles with such attachment flaps cannot, for example, be used when the user is wearing a swimming costume.

Another disadvantage with attachment flaps is that they are relatively cumbersome and require a great deal of dexterity to be able to be fastened in a correct manner about the leg openings of the panties. Particularly with attachment flaps which extend along a long portion of the side edges of an absorbent article, it can be virtually impossible to fold the attachment flaps around the curved leg openings of the panties without chafing and ugly creases being created in the attachment flaps.

To improve the leakage security, it has been proposed in EP 0,067,465 to manufacture a two-piece sanitary napkin in which the two pieces are mutually attached only at their end portions. The lower piece is attached to the user's panties and the upper piece contacts the user's body. It is meant that the pieces, during use, should be able to move somewhat with respect to each other. However, the displaceability between the pieces is greatly restricted and the known sanitary napkin is still dependent on movement of the panties. Furthermore, there is no assurance that the upper piece will be maintained in contact with the user's body during use.

A further two-piece absorbent article is described in PCT/SE96/01061 in which the two pieces are moveable with respect to each other. This known article also has restricted displaceability between the pieces and this is, to a certain extent, dependent on movement of the panties.

With the present invention, however, an improved absorbent article is provided of the type mentioned in the preamble.

SUMMARY OF THE INVENTION

The liquid-impermeable casing layer 5 can be any soft and pliable material with sufficient resistance to liquid penetration. Examples of such materials are thin, flexible plastic films, denser nonwoven material, hydrophobic textile materials or paper layers, liquid-permeable materials with a liquid-impermeable coating, or the like. It is generally no disadvantage if the liquid-impermeable casing layer 5 be gas and vapor permeable since, in this manner, the sanitary napkin exhibits certain breathability, something which contributes to increased comfort during use.

An article in accordance with the present invention is primarily characterized in that the second part of the article is curved in the longitudinal direction and presents high resistance to flexing along flexure lines parallel to the transverse direction of the article, both in a wet and a dry condition, and in that the first part, in a non-influenced condition has a lesser extension in a longitudinal direction than the second part and is provided with at least one elastically extensible region in the longitudinal direction.

The stiffness or the resistance to flexure in the second part must be so high that the tensile forces from the extended first part do not cause breakage or creases in the second part. The stiffness can be attained by lamination of a plurality of components whose combined stiffness is sufficiently high, or by using a particular stiffness-enhancing component such as an insert of rigid plastic or metal.

The second part can be extremely stiff and may for example be made from some sort of metal or hard plastic which remains substantially uninfluenced by the tensile forces from the first part and by those forces which arise during use of the article. Such an extremely stiff second part must be preshaped so that during manufacturing of the article it is provided with a curvature which approximately corresponds to the curvature in the crotch region of the user, from the lower portion of the abdomen backwards towards the bottom.

Even though a static second part may function satisfactorily, it is nevertheless beneficial for several reasons to use a more flexible second part. Thus, the second part can consist of, or comprise, a stiff yet flexible bar, rod or similar elongate shaping element of plastic, metal or the like. Of course, a plurality of such shaping elements may be included in one and the same article, for example a plurality of substantially parallel stiff strips or rods.

Such flexible yet stiff shaping elements can be manufactured in a flat condition and be given a desired curvature at the same time that the first part is attached to the second part. The tensile force in the elastic first part should therefore be adapted to the stiffness of the second part so that the second part, as a result of the pretension in the first part, is given a curvature which substantially corresponds to the curvature in the user's groin. The first part can be attached to the second part by the manufacturer.

Alternatively, the two parts can be separate or only joined at the one end portion when the absorbent article is delivered to the user. This provides the advantage that the article can be packaged in a substantially flat condition, something which makes the article easier to handle and which saves space and packaging material.

According to a preferred embodiment, the first part has at least in each one end portion a lesser extension in the transverse direction than in a region situated between the end portions of the first part, whereby the connection between the first part and the second part has high rotational mobility about a longitudinal axis through the article.

The second part of the absorbent article can be totally non-absorbent or comprise a greater or lesser quantity of absorbent material depending on whether the second part is expected to contribute greatly to the absorption capacity or merely provide extra leakage protection.

The absorbent article is suitably provided with attachment means for attaching the article to the user's panties. For example, the attachment means can be in the form of self-adhesive glue on the second part, over a surface which during use is intended to face towards the user's panties.

Another suitable attachment means which can be used individually or together with adhesive or hook-and-loop type fasteners on the second part of the article are attachment flaps arranged on the side edges of the article. Such attachment flaps are provided on the second part along at least a region of each side edge on the second part, whereby the attachment flaps are intended during use to be folded around the leg openings of the user's panties and are provided with means for attaching the flaps to the outside of the panties. Suitable means for attaching the flaps to the outside of the panties are, for example, glue surfaces, hook-and-loop surfaces, snap fasteners or the like. Furthermore, it is possible to use attachment flaps of the type which automatically clamp themselves about the side edges of the panties. Examples of such attachment flaps are given in WO 92/07537 and WO 92/07536. These documents describe attachment flaps which are arranged on the lower side of an absorbent article with the free ends of the flaps being directed towards the longitudinal centerline of the article. Such attachment flaps work extremely well with a stiff article which is curved in the longitudinal direction since the curvature contributes to maintaining the attachment flaps pressed against the underside of the article.

In accordance with the invention, the first part is elastically extensible. To achieve elastic extensibility, the first part may comprise an elastic member such as an elastic thread, an elastic strip, piece of material or the like which is elastically extensible at least in the longitudinal direction of the article and which is situated at at least the one end portion, in which manner the first part is elastically attached to the second part.

The first part can furthermore comprise one or more elastic members extending along the entire length of the first part.

The absorbent article is advantageously provided with an upraised portion on the first part. The upraised portion is thereby arranged so that it projects from a central portion of the surface on the first part which, during use, is intended to face towards the user.

The constituent parts of the absorbent article can be releasably joined at at least the one end portion. Such releasable joining can be achieved using complementary fastening means such as hooks and loops, buttons and button-holes, snap fasteners, hook-and-loop type surfaces, tie straps or the like.

BRIEF DESCRIPTION OF THE DRAWINGS

The invention will be described in the following in greater detail with reference to the embodiments which are shown in the attached drawings. Thus.

DETAILED DESCRIPTION OF PREFERRED EMBODIMENTS

Figure 1:
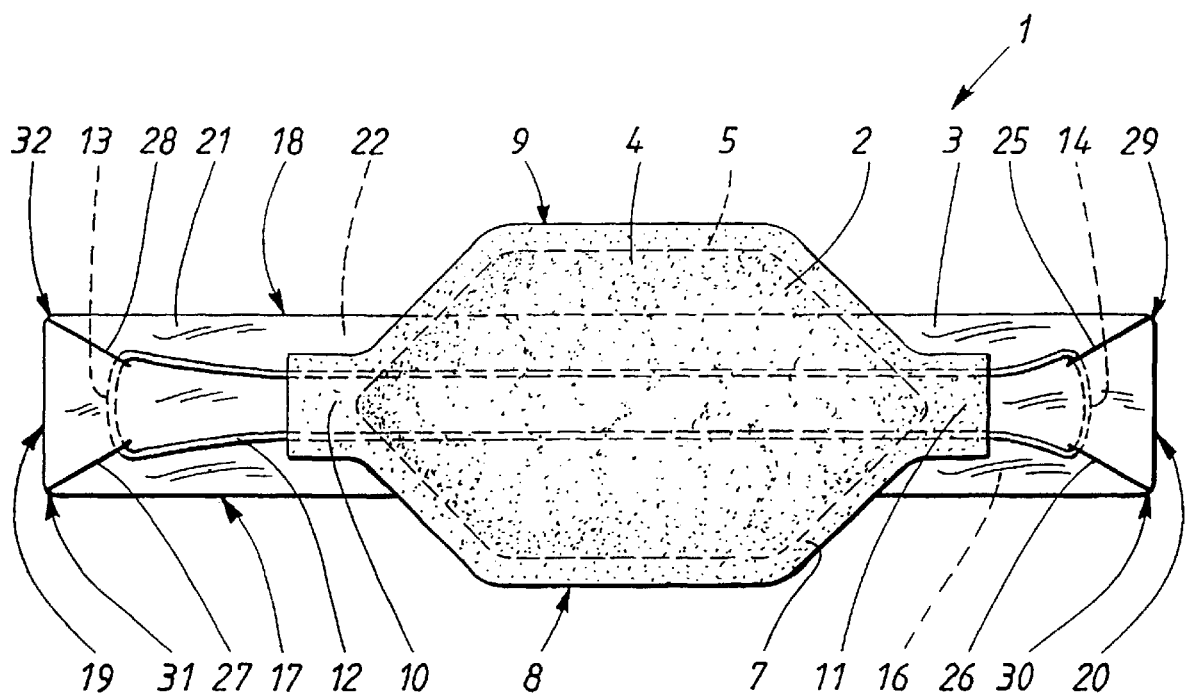
FIG. 1 shows a plan view of a sanitary napkin according to a first embodiment to the invention.
Figure 2:
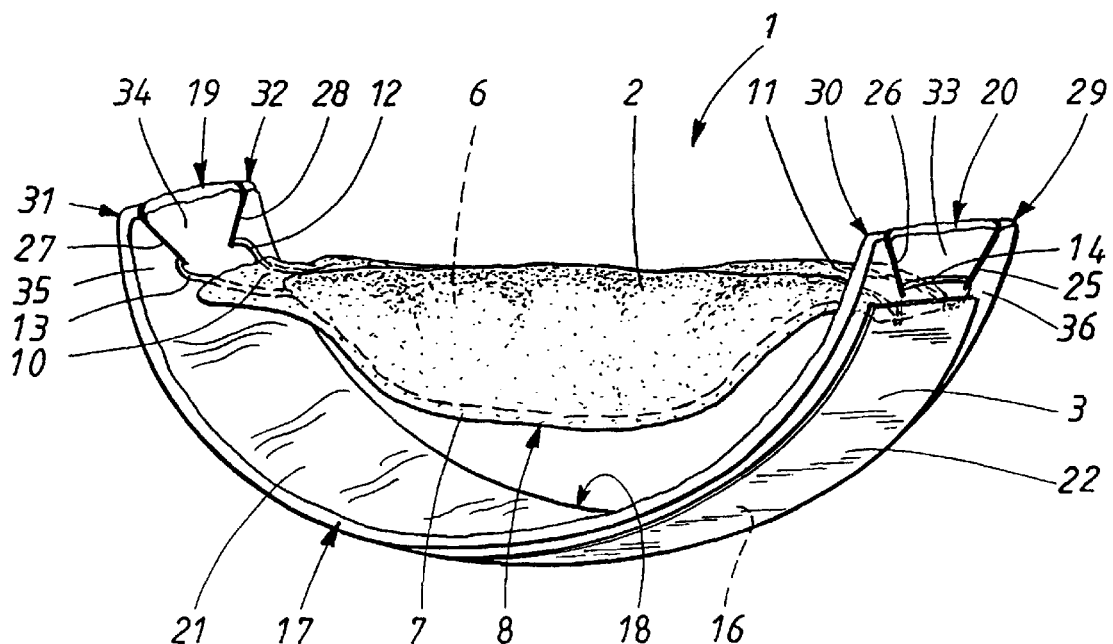
FIG. 2 shows the sanitary napkin of FIG. 1 when in use.

The sanitary napkin 1 shown in FIGS. 1 and 2 is made from two parts 2, 3. The upper part 2 is absorbent and, when the sanitary napkin is used, is intended to contact the user's body and collect and absorb the body fluid which is discharged on the sanitary napkin. The upper part 2 comprises a casing 4, 5 consisting of a liquid-permeable layer 4 which is intended during use to face the user, and a liquid-impermeable layer 5 which during use is intended to face away from the user. The two casings 4, 5 encase an absorbent body 6 which is dimensioned to be able to receive and absorb the discharged body fluid. The casing layers 4, 5 are mutually joined about the absorbent body 6, for example by being glued together or welded around a casing edge 7 projecting from the absorbent body 6.

The liquid-permeable casing layer 4 suitably consists of a soft, skin-friendly and flexible material of a type which is normally used as a surface material in absorbent articles. Examples of such materials are perforated plastic films, nonwoven textiles which are normally termed non-woven material, nets of textile or plastic produced by stitching, crocheting, braiding, moulding or the like, as well as conventional woven textile materials, of course.

The liquid-impermeable casing layer 5 can be any soft and pliable material with sufficient resistance to liquid penetration. Examples of such materials are thin, flexible plastic films, denser nonwoven material, hydrophobic textile materials or paper layers, liquid-permeable materials with a liquid-impermeable coating, or the like. It is generally no disadvantage if the liquid-impermeable casing layer 5 be gas and vapour permeable since, in this manner, the sanitary napkin exhibits certain breathability, something which contributes to increased comfort during use.

The absorbent body 6 can also be of any type suitable for the stated purpose. Thus, the absorbent body 6 can be made from one or more layers of absorbent fibers such as cellulose fluff pulp, rayon, cotton, or the like, as well as tissue material, non-woven material, foam or other absorbent or non-absorbent components.

To increase the absorption capacity, the absorbent body 6 can comprise so-called superabsorbents which are polymer materials, normally in the form of particles, flakes, fibers or the like and which have the ability to absorb several times their own weight of bodily fluid during formation of an aqueous gel. Superabsorbents can be present in the form of one or more layers or regions in the absorbent body 6 or may be mixed with other absorbent material such as cellulose fluff pulp or absorbent fiber waddings of another type. In addition, the superabsorbents can of course be present in a non-absorbing support structure, for example a fibrous layer of non-absorbing fibers.

In the shown example, the upper part 2 of the sanitary napkin 1 has a hexagonal, somewhat elongate shape with two longitudinal side edges, 8, 9, which meet at an angle at each end portion 10, 11 on the upper part 2. Naturally, the invention is not restricted to the shown shape, but instead many other shapes for the upper part 2 are conceivable, such as rectangular, oval, circular, trapezoid, etc.

The upper part 2 is further provided with a longitudinally extending, elastic member 12. The elastic member 12 is in the form of an elastic thread, an elastic strap or the like and made to form a closed loop between the end portions 10, 11 of the upper part 2 such that an eyelet 13, 14 of the elastic member 12 projects from each end portion 10, 11. In addition, the elastic member 12 is arranged on the inside of the liquid-impermeable casing layer 5 between the liquid-impermeable casing layer 5 and the absorbent body 6. The elastic member 12 is advantageously attached to the liquid-impermeable casing layer 5 by being glued or welded, or any other suitable manner. Of course, it is conceivable that the elastic member instead be arranged within the absorbent body 6, on the outside of the liquid-impermeable layer 5 or between the liquid-permeable casing layer 4 and the absorbent body 6.

The upper part 2 is designed to be able to contact the user's genitalia and have sufficient absorption capacity for all discharged bodily fluid to be absorbed by the absorbent body 6.

The lower part 3 of the sanitary napkin comprises a shell 16 of a stiff material, preferably a stiff plastic layer. The material is suitably at least somewhat resilient so that, when bent, it endeavours to return to its flat form. The stiff material must be sufficiently flexible in the longitudinal direction of the sanitary napkin so that the shell 16, during use, can be made to bend so that the lower part 3 adopts the curvature on the inside of the user's panties.

The lower part 3 has a substantially rectangular shape with two longitudinal side edges 17, 18 and two transverse end edges 19, 20. The lower part 3 is relatively narrow in relation to its length and has a width which is suitably between 1 and 4 cm and preferably about 3 cm. Measurements have shown that there is a space-limiting, critical region in the groin region between two muscle groups which extend from the inside of the abdominal floor down each thigh. The distance between the two muscle groups in the genital area has been shown to be surprisingly similar in all people, irrespective of body shape and corpulence. Thus, the distance between a user's thighs is of course affected by fatness, whilst the distance between the muscle groups in the user's groin is substantially the same irrespective of whether the user is slim, of normal weight or overweight.

It has been shown by measurements that that which determines whether a user experiences discomfort in the form of pressure or chafing on the insides of the thighs is whether the absorbent article during use has a width which, in the critical region, obviously exceeds the distance between the muscle groups in the groin region. This distance has been shown to be between 30 and 35 mm. It has furthermore been shown that an article having a width which, during use, exceeds 40 mm in the critical region was regarded by many users as being uncomfortable to wear. However, that an absorbent article was pressed towards or projected under the fatty tissue which can be present in the groin region was rarely regarded as uncomfortable.

With conventional absorbent articles, the restricted space in the user's crotch implies that the article is compressed in an uncontrolled manner between the user's legs and becomes folded so as to be able to be accommodated in the groin. Should some component of the absorbent article have such a stiffness, however, that it cannot easily be compressed by the forces which normally arise during use, the compression can of course only take place to a restricted extent. For reasons of comfort, therefore, it is important that the width of the absorbent article in the mid portion during use does not exceed the critical value which can be tolerated by the user. A certain controlled compressibility can be achieved by providing the article with deformable zones. Such deformable zones can for example be in the form of soft edges, longitudinally extending material folds or material weakenings such as holes, thinner material regions or the like.

It is, of course, the width of the article during use which is relevant for the determination of whether or not the risk of chafing arises. Soft components which are deformed during use do not therefore contribute to the same extent to the width of the article during use as relatively non-deformable components would do.

The material which is used for the stiff shell 16 is advantageously so stiff that it is not deformed in the transverse direction by the compressive forces which arise between the user's thighs. It is therefore important that the width of the stiff shell 16, at least within the portion which during use is intended to be positioned in the critical region between the user's legs, does not exceed 40 mm and preferably does not exceed 35 mm.

To reduce the risk of chafing from the edges of the stiff shell 16 in the lower part 3, the shell is dressed with a layer 21 of soft, padded material, such as foam plastic, wadding or similar. If it is deemed to be suitable, the padded material can be encased in a (not shown) outer casing of nonwoven material, or the like.

In the shown embodiment, no absorbent material is present in the lower part 3. Normally, all discharged bodily fluid will be collected and absorbed by the upper part 2. However, this does not exclude the possibility of also providing the lower part with certain restricted absorption capacity. An absorbent lower part can thus collect that bodily fluid which for some reason happens to flow over the edges of the upper part and thus impinge the lower part. Furthermore, an absorbent lower part can be used as a sole absorbent article by a user who only needs reduced absorption capacity, for example towards the end of a menstruation period.

Figure 3:
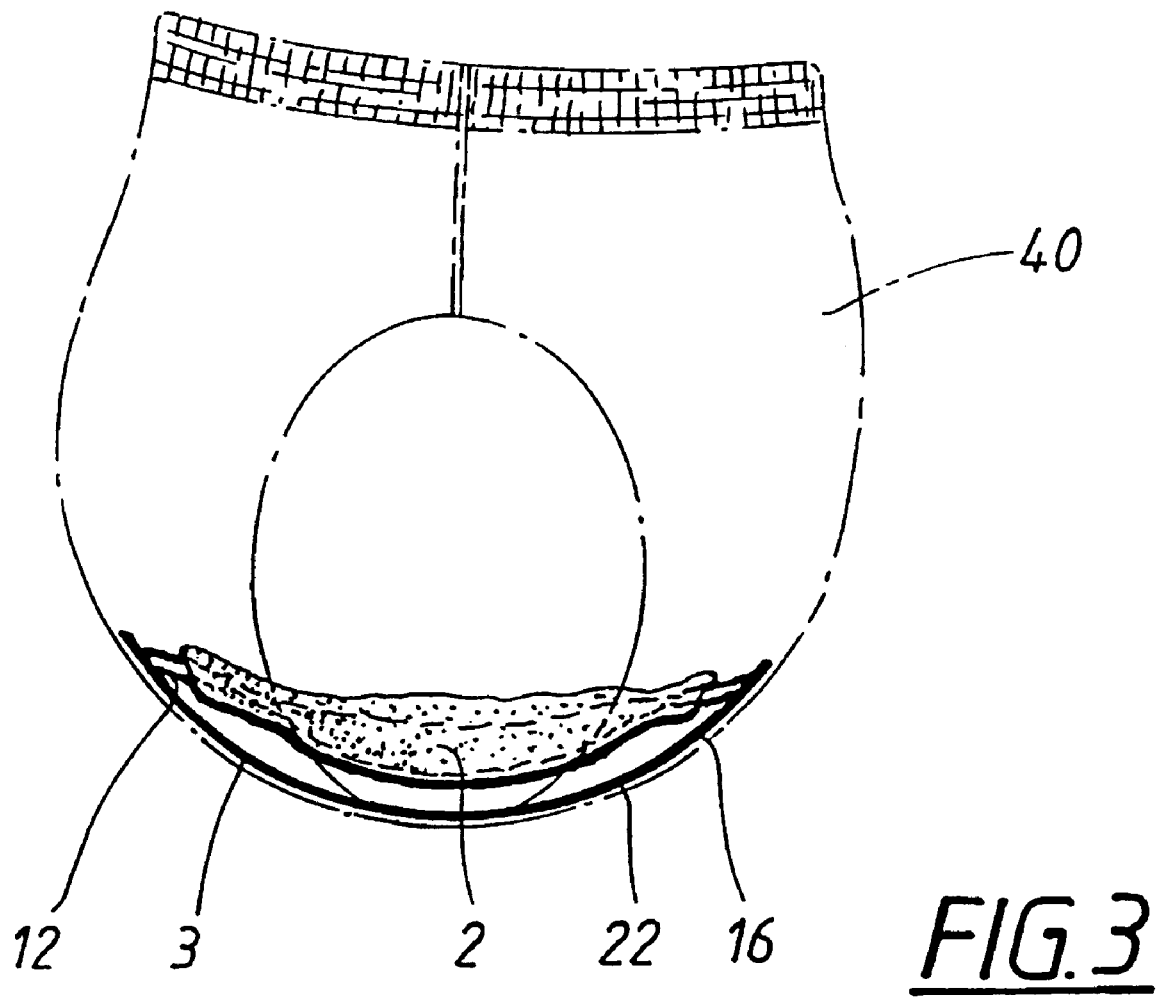
FIG. 3 shows the sanitary napkin of FIGS. 1 and 2 placed within a pair of panties and FIG. 4 shows a plan view of a sanitary napkin according to a second embodiment of the invention.

It is thus conceivable that a user initially makes use of the possibility to use the sanitary napkin shown in FIGS. 1–3 having both the upper part 2 and the lower part 3. Thereafter, the upper part 2 can be removed from the lower part 3 and discarded while the lower part 3 remains in the panties and is used on its own or with a new upper part 2.

The lower part 3 is provided with attachment means 22 in the form of a coating of adhesive on the side of the lower part 3 which, during use, is intended to face towards the user's panties. In the shown example, the adhesive coating covers almost the entire surface of the lower part, which ensures that the lower part 3 is securely retained in the panties during use. Only the end portions 435, 436 of the lower part are free of adhesive in order to facilitate exchange of the upper part 3.

It is of course possible to imagine that only restricted regions of the surface of the lower part 3 facing the panties be coated with adhesive. The disadvantage therewith is, however, that the risk that the lower part comes loose from the panties is relatively great due to the forces which arise in the stiff material in the lower part. Alternative ways of attaching the lower part in the panties are also conceivable. For example, the lower part 3 can be provided with attachment flaps of a conventional type extending from the side edges, which flaps are intended to be folded around the leg openings of the user's panties and fastened to the outside of the panties. Furthermore, different types of mechanical fastening members, such as snap fasteners, clips or the like, can be used individually or in combination with, for example, adhesive attachment means.

A notch 25–28 is cut into the end portions 35, 36 of the lower part 3, or cut from each corner 29–32 of the lower part 3. The notches extend a distance obliquely in from the corners and create a suspension flap 33, 34 at each end portion 35, 36. When the sanitary napkin 1 is in use, it is intended that the eyelets 13, 14 created by the elastic member 12 on the upper part 3 are brought over the suspension flaps 33, 34 so that the end portions 10, 11 of the upper part 2 are connected to the lower part 3 at the end portions 35, 36 of the lower part 3. Thus, the length of the elastic member 12 is to be chosen such that, in its non-extended state, the elastic member 12 is shorter than the planar distance between the end portions 35, 36 of the lower part 3. In this manner, the elastic member 12 will endeavour to bend the stiff shell 16 in the lower part 3. Suitably, the tensile force in the elastic member 12 is adapted to the bending resistance of the stiff shell 16 so that the resulting curvature of the stiff shell 16 is similar to the curvature which can be expected to be present within the user's panties. Small deviations from the actual curvature within the user's panties are compensated for during use by the forces between the panties and the user's body.

The pretension in the elastic member 12 depends on how stiff the shell 16 is. Nevertheless, it will be quite simple to arrive at a suitable pretension in each case by trials to attain the desired curvature of the stiff shell 16.

Since the upper part 2 is in a pretensioned condition between the end portions of the lower part 3, the sanitary napkin adopts the appearance shown in FIG. 2. The upper part 2 is thus suspended between the end portions of the lower part 3 with a gap between the two parts 2, 3. During use, the upper part 2 is maintained in resilient contact against the user's body by means of the elastic member 12 endeavouring to return to its unloaded contracted state.

The pressure from the wearer's panties, together with the tensile forces in the elastic member 12, prevent the stiff shell 16 from adopting its flat condition. When the user's body presses against the liquid-permeable casing layer 4 on the upper part 2, the sanitary napkin will not therefore flatten out. Instead, that which initially happens is that the distance between the two parts 2, 3 reduces. In the reverse manner, the distance between the parts 2, 3 increases when the pressure from the user's body is reduced or ceases. Thus, the anatomic fit of the sanitary napkin is automatically and continuously adjusted during use.

The construction of the sanitary napkin with two parts 2, 3 which can be separated by unhooking the eyelets 13, 14 on the upper part 2 from the suspension flap on the lower part 3 is advantageous for many reasons. For example, it is possible to package the sanitary napkin in a disassembled state which implies that it is flat in the package. This is a considerable advantage both in terms of space-saving and cost.

If so desired, the lower part can also be used more than once, something which implies both material savings and which makes the sanitary napkin easier to use.

Since the upper part 2 is small and convenient, individual upper parts can be easily and discretely carried in a pocket or handbag.

Since, in accordance with the invention, the absorbent part of the sanitary napkin is always maintained in the correct position in relation to the user's body orifices during use, the risk of leakage is minimal. This implies that the absorbent part 2 can be made to have a relatively small absorption capacity and still offer sufficient absorption. A sanitary napkin according to the invention is thus very economic with material since the stiff second part 3 can be reused one or more times and since no unnecessary material needs to be used in the first absorbent part 2.

In FIG. 3 it is shown how the sanitary napkin behaves during use. The sanitary napkin is attached in the crotch portion to a pair of panties 40 by means of the adhesive attachment means 22. The forces which arise between the panties and the user's body coact with the elastic member 12 and the stiff shell 16 so that the absorbent upper part 2 is continuously held in contact with the user's body. The distance between the upper part 2 and the low part 3 varies during use depending on the movement and body position of the user. When the user sits down, the parts 2, 3 are pressed together so that they contact each other. When the user gets up, the pressure between the panties and the user's body reduces, which results in a gap being formed between the two parts of the sanitary napkin.

Figure 4:
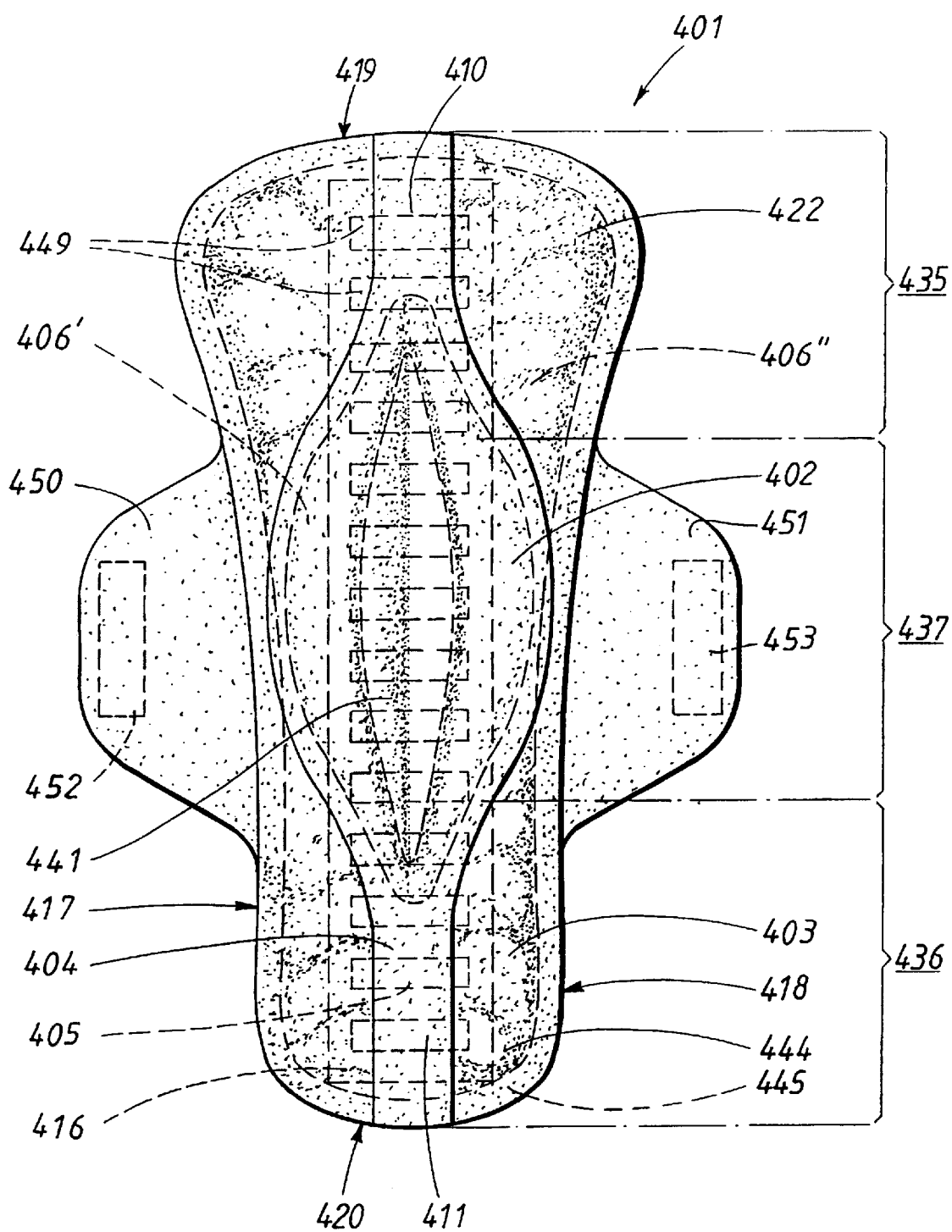

The sanitary napkin 401 shown in FIG. 4 is also made from two parts, an upper part 402 and a lower part 403. That which primarily distinguishes the sanitary napkin of FIG. 3 from the sanitary napkin in FIGS. 1 and 2 is that both the upper part 402 and the lower part 403 comprise absorbent material.

The sanitary napkin 401 thus comprises a first absorbent body 406' in the upper part 402 encased between two liquid-permeable casing layers 404,405, as well as a second absorbent body 406" in the lower part 403 encased between a liquid-permeable casing layer 444 and a liquid-impermeable casing layer 445. The liquid-impermeable casing layer 445 is thereby located above the surface of the second absorbent body 406" which, during use of the sanitary napkin, is intended to face the user's panties and is provided with an attachment means 422 in the form of self-adhesive glue or a friction coating.

As is apparent from FIG. 4, the outermost contours of the sanitary napkin 401 are determined in the plane of the lower part's 403 shape. The lower part 403 and thereby the sanitary napkin in general in a flat condition has a substantially trapezoid shape with two longitudinal side edges 417,418 and two transverse end edges 419,420. The sanitary napkin 401 and the lower part 403 can be divided in a longitudinal direction into a central crotch portion 437 and two end portions 435,436. The forward portion 435, i.e. the end portion which during use is intended to face forwards on the user, is thus somewhat wider than the crotch portion 437 which, in turn, is wider than the rearward portion 436 which is the end portion which is intended to face backwards on the user during use. The first absorbent body 406' occupies about half the length of the sanitary napkin and is widest in the sanitary napkin's crotch portion 437 and becomes narrower towards the end portions 435,436. The first absorbent body 406' further comprises a centrally placed longitudinally extending raised portion 441 which projects from the surface of the upper part 402 which is intended during use to face the user. The raised portion 441 is adapted to the user's anatomy and thus has a shape and size which fits to the space in the genital region of the user. The raised portion 441 is wider at its base, i.e. at the part facing away from the user, than at its peak. Furthermore, the raised portion 441 is widest in its central portion and narrows off in a direction towards the end portions 435,436 of the sanitary napkin.

During use, it is intended that the raised portion 441 shall contact the user's body and ensure that discharged bodily fluid is collected as soon as it leaves the body. In this manner the risk of leakage is minimized.

The upper part 402 has strip-shaped end portions 410,411 formed from portions of the two liquid-permeable casing layers 404,405 of the upper part 402. One of the casing layers 404,405 is elastically extensible, whilst the other casing layer is extensible or elastically extensible. In this manner, the two strip-shaped end portions 410,411 are elastically extensible.

The lower part 403 comprises a rigid, elastic ladder-shaped insert 416 which is preferably situated within the second absorbent body 406" or between the second absorbent body 406" and the liquid-impermeable casing layer 445 of the lower part 403. For the same reasons as for the sanitary napkin in FIGS. 1–3, the width of the ladder-shaped insert 416 should not exceed 40 mm. Since the insert 416 is not solid, but has a number of rectangular openings 449 passing therethrough, the resistance of the insert 416 to compression in the transverse direction is however less than that of the stiff shell 16 shown in FIGS. 1–3. Certain adjustments to the width of the insert 416 can thus be obtained during use without the user experiencing chafing or other discomfort.

The lower part also comprises two attachment flaps 450, 451, each provided with attachment means 452,453, for example an adhesive or a hook-and-loop type surface. During use, the attachment flaps 450,451 are folded around the leg openings of the user's panties and fastened by means of the attachment means 452,453 to the material on the outside of the panties. Attachment flaps of this type serve many functions. On the one hand, they ensure that the sanitary napkin sits tightly in the panties and, on the other hand, they maintain the lower part 403 of the sanitary napkin stretched out between the panties' leg openings and thus counteract deformation. In addition, the attachment flaps 450,451 cover the panties' leg edges and thereby themselves act as edge leakage protection.

The upper part 402 is fixedly attached to the lower part 403 at the respective end portions 410,411;435,436 of the parts. This can be achieved by, for example gluing, stitching or welding with heat or ultrasound.

The sanitary napkin 401 is shown in FIG. 4 in a flat condition. This implies that the shown sanitary napkin has been stretched out so that the constituent components can be shown more clearly. Since the upper part 402 is fixed to the lower part 403 with the elastically extensible end portions 410, 411 stretched out, the sanitary napkin will adopt a shape similar to that shown in FIG. 2 when it is not subjected to external forces. The end portions 410, 411 of the upper part 402 contract and endeavour to return to their non-influenced condition. This implies that the lower part 403 becomes curved in the longitudinal direction and adopts a curvature which is suitably adapted so that it lies close to the corresponding curvature of the user's body in the genital region.

Since the strip-like elastic end portions 410, 411 of the upper part 402 are relatively wide, good rotational stability of the upper part is attained. In this manner, the risk that the upper part during use rotates about the attachment regions and thus ends up upside-down by mistake is minimal. Suitably, the width of the strip-like end portions 410, 411 is at least 20% and preferably between 25 and 50% of the width of the upper part 402 at the widest location. A certain rotational mobility of the upper part is however desirable since this contributes to the sanitary napkin's ability to adapt itself to the anatomy of the user and her body movements. Even though the invention also includes absorbent articles in which the upper part has approximately the same width over its entire length and absorbent articles having an upper part which has substantially the same width as the lower part, such embodiments are less preferred since the rotational mobility of the upper part is restricted if the attachment between the two parts is very wide.

The invention is not intended to be restricted to the embodiments described herein; instead a number of further variations and modifications are possible within the scope of the appended claims. In addition, the invention includes all conceivable combinations of the described embodiments.

What is claimed is:

1. An absorbent article comprising:

a first absorbent part and a second part;

both the first absorbent part and the second part having a substantially elongate shape with a longitudinal direction and a transverse direction;

each part comprising two end portions;

said first absorbent part being suspended in a pretensioned condition between the end portions of the second part whereby the two parts are mutually joined solely at their end portions;

the second part being curved in the longitudinal direction and having resistance to flexure along flexure lines parallel to the article's transverse direction in both a wet and dry condition;

the first absorbent part being narrower at its end portions than in a middle portion thereof, and having a length which is less than the length of the second part when both parts are in a relaxed state; and said first absorbent part having at least one region which is elastically extensible in the longitudinal direction.

2. An absorbent article comprising:

a first absorbent part and a second part;

both the first absorbent part and the second part having a substantially elongate shape with a longitudinal direction and a transverse direction;

each part comprising two end portions;

said first absorbent part being suspended in a pretensioned condition between the end portions of the second part whereby the two parts are mutually joined solely at their end portions;

the second part being curved in the longitudinal direction and having resistance to flexure along flexure lines parallel to the article's transverse direction in both a wet and dry condition;

the first absorbent part having a length which is less than the length of the second part when both parts are in a relaxed state;

said first absorbent part having at least one region which is elastically extensible in the longitudinal direction; and said first absorbent part having a transversely widest region situated between the end portions of the first absorbent part.

3. The absorbent article according to claim 2, wherein the second part comprises absorbent material.

4. The absorbent article according to claim 2, wherein the second part comprises a stiffening member.

5. The absorbent article according to claim 4, wherein the stiffening member is a plastic insert.

6. The absorbent article according to claim 4, wherein the stiffening member is ladder-shaped.

7. The absorbent article according to claim 2, wherein the second part is curved in the longitudinal direction when in the relaxed state.

8. The absorbent article according to claim 2, wherein the second part in the relaxed state has a substantially flat shape, though under the influence of tensile forces which are present in the pretensioned attached first absorbent part, adopts a curved shape in the longitudinal direction.

9. The absorbent article according to claim 2, wherein the second part has a first surface which in use faces panties of a user and a second surface which in use faces the user; said first surface being provided with attachment means in the form of self-adhesive glue.

10. The absorbent article according to claim 2, wherein the second part comprises two side edges extending in the longitudinal direction, and attachment flaps arranged on the second part along at least a portion of each side edge of the second part, whereby the attachment flaps are intended during use to be folded about leg openings of panties of a user, and are provided with means for fastening the flaps to the outside of the panties.

11. The absorbent article according to claim 2, wherein the first absorbent part has an elastic member which is elastically extensible in the longitudinal direction of the article, and is arranged at at least one end portion of the first absorbent part, whereby the first absorbent part is elastically suspended on the second part.

12. The absorbent article according to claim 2, wherein the first absorbent part comprises one or more elastic members extending along the entire length of the first absorbent part.

13. The absorbent article according to claim 2, wherein the first absorbent part comprises a first surface which faces towards the second part, and a second surface, which in use, is intended to face a user, whereby an upraised portion projecting from the second surface is situated centrally on the first absorbent part.

14. The absorbent article according to claim 2, wherein the first absorbent part and the second part of the article are releasably attached at least at one end portion.

15. The absorbent article according to claim 14, wherein the releasable attachment is in the form of cooperating attachment means.

16. The absorbent article according to claim 15, wherein at least one end portion of the first absorbent part is provided with an eyelet and a corresponding end portion of the second part comprises a hook or groove for cooperation with the eyelet.

17. The absorbent article according to claim 2, wherein the first absorbent part is fixedly attached to the second part at at least one end portion by one of gluing, welding, and stitching.

* * * * *